(12) United States Patent
Stouffs et al.

(10) Patent No.: US 7,955,438 B2
(45) Date of Patent: Jun. 7, 2011

(54) PROCESS FOR PREPARING ALKALI AND HEAT STABLE POLYOLS

(75) Inventors: Robert Henri-Marcel Stouffs, Ferrara (IT); Simonetta Zerbinati, Rovigo (IT)

(73) Assignee: Cargill, Incorporated, Wayzata, MN (US)

( * ) Notice: Subject to any disclaimer, the term of this patent is extended or adjusted under 35 U.S.C. 154(b) by 293 days.

(21) Appl. No.: 12/097,476

(22) PCT Filed: Nov. 28, 2006

(86) PCT No.: PCT/EP2006/068971
§ 371 (c)(1),
(2), (4) Date: Jun. 13, 2008

(87) PCT Pub. No.: WO2007/068578
PCT Pub. Date: Jun. 21, 2007

(65) Prior Publication Data
US 2008/0302358 A1  Dec. 11, 2008

(30) Foreign Application Priority Data

Dec. 16, 2005 (EP) .................................. 05257793

(51) Int. Cl.
*C13K 13/00* (2006.01)
*C07H 1/00* (2006.01)
*C07H 3/00* (2006.01)
*C08B 37/00* (2006.01)
*C07C 35/14* (2006.01)
*C07C 35/16* (2006.01)

(52) U.S. Cl. ........ 127/42; 127/46.1; 127/46.2; 536/124; 568/833

(58) Field of Classification Search ............... 127/42, 127/46.1, 46.2; 536/124; 568/833
See application file for complete search history.

(56) References Cited

U.S. PATENT DOCUMENTS

| 3,040,104 | A | * | 6/1962 | Sarappo et al. | 568/872 |
|---|---|---|---|---|---|
| 5,773,604 | A | * | 6/1998 | Lefevre et al. | 536/104 |
| 6,417,346 | B1 | * | 7/2002 | Salome et al. | 536/104 |
| 6,451,123 | B1 | * | 9/2002 | Saska et al. | 127/46.2 |
| 7,179,336 | B2 | * | 2/2007 | Van Lancker | 127/46.2 |

FOREIGN PATENT DOCUMENTS

| EP | 0 711 743 |   | 6/1999 |
|---|---|---|---|
| EP | 1 095 925 |   | 8/2003 |
| JP | 63-079844 |   | 4/1988 |
| JP | 07-145090 | * | 6/1995 |
| WO | WO 03/066553 |   | 8/2003 |
| WO | WO 2004/058671 |   | 7/2004 |

OTHER PUBLICATIONS

Murphy et al., "A reversible reaction between reducing sugars and a weak-base anion-exchange resin," *Carb. Res.*, 1968, 7:460-467.

* cited by examiner

*Primary Examiner* — Patricia L Hailey
(74) *Attorney, Agent, or Firm* — Fish & Richardson P.C.

(57) ABSTRACT

The current invention relates to a continuous process for preparing heat an alkali stable polyol composition. Alkali is added to the feed of the anion exchange resin and is allowing running the resin battery in full service mode.

15 Claims, No Drawings

PROCESS FOR PREPARING ALKALI AND HEAT STABLE POLYOLS

CROSS-REFERENCE TO RELATED APPLICATIONS

This application is a National Stage application under 35 U.S.C. §371 and claims benefit under 35 U.S.C. §119(a) of International Application No. PCT/EP2006/068971 having an International Filing Date of Nov. 28, 2006, which claims the benefit of priority of EP 05257793.9 having a filing date of Dec. 16, 2005.

TECHNICAL FIELD

The current invention relates to a continuous process for preparing alkali and heat stable polyols, in particular sorbitol and/or maltitol.

BACKGROUND OF INVENTION

Alkali and heat stability of polyols are important in a number of industrial and food applications. The confectionary, pharmaceutical and oral and dental hygiene industries and even chemical industries use polyol compositions, which are highly chemically stable in alkaline medium.

EP 0 711 743 describes the preparation of alkaline and heat stable polyol compositions wherein the stabilisation is either obtained through fermentation, oxidation or caramilisation.

EP 1 095 925 describes an alkali and heat stabilisation treatment. After this treatment the polyol is subjected to a purification step with at least one passage over a strongly acid cationic resin at a temperature below 30° C.

In JP 63079844, a method is described in which an aqueous sugar alcohol solution is adjusted to a pH-value of between 8 and 13, followed by a (discontinuous) heating step at temperatures varying between 90° C. and 220° C. The resulting product is then purified by passing the polyol solution through a strong acidic cation exchange resin, a strong anion exchange resin and a mixed bed resin.

WO 03/066553 describes a method for preparing alkali and heat stable polyols and the purification step involves a double passage over a cationic, anionic ion-exchanger configuration (CACA), comprising at least a first weak acid cationic ion exchanger resin and a second strong, medium or weak alkaline anionic ion-exchanger resin.

WO 2004/058671 describes a process for preparing alkali and heat-stable polyols by treatment with a strong anion exchange resin in the hydroxide form. In a multiple column-system at least part of the columns of the system are used in the regeneration mode, while the remaining columns are used in a service mode.

Currently there is a need for a simple, cost-effective process which allows obtaining alkali and heat stable polyols and the current invention provides such a process.

SUMMARY OF INVENTION

The current invention relates to a continuous process for preparing alkali- and heat-stable polyol compositions and said process comprises the following steps:
a) taking an aqueous solution of a polyol composition comprising polyols and y % of reducing sugars based upon the dry substance of the polyol composition,
b) adding to the aqueous solution an effective amount of alkali,
c) feeding the aqueous solution to a resin battery comprising an anion exchange resin for obtaining an aqueous polyol composition comprising polyols and x % of reducing sugars based upon the dry substance of the polyol composition, and wherein $x<y$, d) collecting the aqueous polyol composition comprising polyols and x % of reducing sugars based upon the dry substance of the polyol composition.

The current invention relates to a process wherein y is from 0.040% to 0.100% based on dry substance of polyol composition.

The current invention relates to a process wherein x is not more than 0.015% based on dry substance of polyol composition, preferably not more than 0.010%.

The current invention further relates to a process wherein the resin battery further comprises a cationic resin and a polisher resin. Furthermore the anion exchange resin is a strong base anion exchange resin in the hydroxide form. The temperature of the resin battery is from 70 to 100° C., preferably from 75 to 95° C., more preferably from 85 to 90° C.

The current invention relates to a process wherein the aqueous polyol composition, comprising polyols and x % of reducing sugars based upon the dry substance of the polyol composition, is increased in dry substance. In a preferred embodiment, the polyol is sorbitol and/or maltitol.

The current invention relates to a process wherein the volume throughput is between 0.2 and 1 BV/hour. Furthermore it relates to a process wherein the resin battery is running for at least 30 days without any regeneration of the resins.

DETAILED DESCRIPTION

The current invention relates to a continuous process for preparing alkali- and heat-stable polyol compositions and said process comprises the following steps:
a) taking an aqueous solution of a polyol composition comprising polyols and y % of reducing sugars based upon the dry substance of the polyol composition,
b) adding to the aqueous solution an effective amount of alkali,
c) feeding the aqueous solution to a resin battery comprising an anion exchange resin for obtaining an aqueous polyol composition comprising polyols and x % of reducing sugars based upon the dry substance of the polyol composition, and wherein $x<y$, d) collecting the aqueous polyol composition comprising polyols and x % of reducing sugars based upon the dry substance of the polyol composition.

The polyol is having typically the following chemical formula $C_nH_{2n+2}O_n$, which corresponds to a hydrogenated carbohydrate.

Typically, the polyol is selected among the tetritols, pentitols, hexitols, polyols from disaccharides, polyols from oligosaccharides, polyols from polysaccharides, and mixtures thereof.

The disaccharides are in most cases maltose, isomaltulose, maltulose, isomaltose and lactose, which, by hydrogenation, produce maltitol, isomalt, isomaltitol and lactitol. Oligosaccharides and polysaccharides, which are products of increasingly high molecular weight usually originate from an acidic and/or enzymatic hydrolysis of starches and/or tuber starches, of xylans or of fructans like inulin, but can also be obtained by acidic and/or enzymatic recombination of mono- or disaccharides such as those referred to above.

More specifically the polyol can be selected from the group consisting of erythritol, threitol, arabinitol, xylitol, ribitol, allitol, altritol, gulitol, galactitol, mannitol, sorbitol, talitol, maltitol, isomaltitol, isomalt, lactitol, and mixtures thereof. Preferably the polyol is sorbitol and/or maltitol.

Alkali- and heat stability of sugar alcohols (=polyols) are important in a number of industrial and food applications, that is to say in any application which requires resistance in alkaline medium and/or heat resistance against formation of undesirable colour and/or taste formation. Alkali- and heat-stability of sugar-alcohols is important in all those applications where colour and/or off-taste formation under these conditions must be prohibited. This is the case, e.g. where polyol compositions are used as humectants in toothpastes containing alkaline abrasives, as building blocks of polyether polyols, or as starters for preparing sorbitan esters. Colouring of end-products containing these polyols is often due to the presence of colour-forming precursors, such as for example the residual reducing sugars being present in the polyol compositions used. Furthermore, the colour formation is accelerated by the temperature to which the polyol is exposed.

A phenomenon of yellowing of these compositions at high temperature is also observed when they are employed in the manufacture of boiled sugars. Such a colouring is often incompatible with some flavourings in sweets.

It even happens that polyol compositions are set aside from the manufacturing processes where heat and alkali stability are required because of the unwanted colour formation. Furthermore it has been observed that it is preferable to have these polyol compositions made available as non-crystallisable polyol syrups. Non-crystallisable polyol syrup has to be understood to mean in the current invention a composition of polyols which forms a syrup that is not crystallizing at 20° C., at a dry matter content of 70% when stored in a airtight closed vessel for one month.

Based on this knowledge, there is a need for having a simplified process for preparing alkali and/or heat stable polyol compositions.

Surprisingly, the process of the current invention provides this solution by adding an effective amount of alkali to the aqueous solution of the polyol composition and submitting it to an anion exchange resin.

In a preferred embodiment, the aqueous solution of the polyol composition is obtained by the catalytic hydrogenation of the corresponding carbohydrate solution. The catalytic hydrogenation is carried according to what is known, by applying hydrogenation catalysts, such as Raney catalysts, Raney nickel, other catalysts suitable for the hydrogenation of carbohydrates. The hydrogen pressure is between 30 to 150 bar, at a temperature of between 120 to 150° C. The hydrogenation is continued until the residual reducing sugars (measured according to the copper method) is reaching a level of y %. In a more preferred embodiment, the current invention relates to a process wherein y is from 0.050% to 0.300%, preferably from 0.040% to 0.100% based on dry substance of polyol composition. By running the catalytic hydrogenation in such a way, the process is economical viable and no long residence times are required in order to reduce the residual reducing sugar levels further down.

Surprisingly, it is observed that by adding an effective amount of alkali, preferably from 0.1 to 0.5%, more preferably from 0.1 to 0.2% based upon the dry substance of polyol composition, the aqueous solution of the polyol composition can be applied onto an anion exchange resin which is in full service mode.

The alkali is none limiting, but preferably sodium hydroxide is applied. The alkali can be applied in dry form or can be added as an aqueous solution.

The total reducing sugar content after complete hydrolysis is varying from 3.5 to 98%, as determined my means of Copper method, this has to be understood by the fact that after complete hydrolysis, polyols as for example maltitol is split into glucose and sorbitol, whereby the glucose is contributing to the percentage measured by the Copper method. The current invention is also applicable to higher polyols such as polyols from disaccharides, polyols from oligosaccharides, polyols from polysaccharides, and mixtures thereof.

Finally it is important to obtain heat and/or alkali stable polyol compositions, this is in particular true for compositions which contain not more than 0.040%, preferably not more than 0.030%, more preferably not more than 0.020%, not more than 0.015%, most preferably not more than 0.010% reducing sugars based on dry substance of polyol composition (is the value of x in the polyol composition).

In a preferred embodiment, the process is so efficient that x is not more than 10% of y, more preferably x is not more than 5% of y, meaning that due to the process of the current invention 90 to 95% of the residual reducing sugars are removed. These polyol compositions are extremely alkali- and heat stable in the aforementioned industrial and food applications.

The current invention relates to a continuous process wherein the columns are in full service mode. The inventors surprisingly have found that by adding an effective amount of alkali, there is no need for running part of the resin battery in regeneration mode. Due to the fact that the resin battery is in full service, less alkali is consumed and actually up to 50% of the total consumption of alkali is saved up. In order to benefit from all the potentials of this process, the preferred anion resin is a strong base anion exchange resin in the hydroxide form. The strong base anion exchange resin preferably belongs to one of the categories:

the thermally stable-type category;
the styrenic type I, II, III
the acrylic resin type.

A typical example of a suitable thermally stable strong anion exchange resin is Dowex MSA-1 (Dow), with quaternary ammonium functional groups. Similar resins, having the same properties but provided by another supplier are applicable as well. The strong anionic resin is designed to remove anions (organic and/or inorganic).

The current invention further relates to a process wherein the resin battery further comprises a cationic resin and a polisher resin. The cationic resin is carrying a functional group of the sulphonic $SO_3H$ type and is preferably a strong acidic cationic resin. A suitable example is Lewatit S 25 28 and the like. The strong cationic resin is designed to remove the cations such as in particular the cations provided by the alkali such as sodium ions from sodium hydroxide, as well as residual ions from the hydrogenation catalysts, such as nickel ions.

The polisher resin is an adsorbent specially designed for decolourization as well as taste and odour removal. A suitable example is Dowex Optipore SD-2 and the like.

The process of the current invention is not limited by the temperature, but preferably the temperature of the resin battery is from 70 to 100° C., preferably from 75 to 95° C., more preferably from 80 to 90° C.

In a preferred process according to the invention, the polyol composition is fed to a column-system containing a strong anion exchange resin in the hydroxide form with a volume throughput of $\leq 5$ bed volumes (BV)/hour, preferably a volume throughput of $\leq 3$ bed volume (BV/hour). In a more preferred process according to the invention, the volume throughput is between 0.2 and 1 BV/hour. Most preferably, the volume throughput is between 0.2 and 0.8 BV/hour.

"Bed volume" is hereby defined as the total volume of anionic exchange resin used during the stabilisation step. When a multiple column-system is used, all the columns of the system are used in service mode, comprising the steps of stabilisation and simultaneous decolourisation. An advantageous continuous multiple column-system for this invention is known as an ISEP- or as a CSEP-configuration.

In a preferred process according to the invention, said polyol composition has a pH-value between 10 and 11.5 when sorting from the strong anion exchange resin. The purpose of the invention is furthermore to provide a polyol composition which has a good alkali- and heat stability. The polyol composition obtainable according to the current process are particularly suitable in the preparation of products having an alkaline pH, such as in particular toothpastes based on sodium bicarbonate, antacid compositions, shaving foams, depilatory creams, or for the manufacture of products at high temperatures. The current invention is showing the following significant advantages:

- saving of minimum 50% NaOH consumption,
- contact time in column is very low
- very low colour, less impact for refining
- no loss of production for stream and start/stop
- continuous process
- the stabilisation and purification of the polyol composition is occurring in one step.
- the resin battery is in full service mode.

Surprisingly, the current invention has demonstrated that first of all the process does not need a separate process step in addition to the normal purification step. The stabilisation can be included in a normally required purification or demineralisation step, provided that an effective amount of alkali is added to the solution of the polyol composition before submitting it onto the anion exchange resin. This addition of the effective amount of alkali allows running a continuous process on a resin battery in full service. The usual part of the resin battery reserved to regeneration is no longer needed, thus increasing production capacity and further reducing the amount of chemicals such as alkali.

The invention is further illustrated by reference to the following examples describing in detail the process of the current invention. The invention described and claimed herein is not to be limited in scope by the specific embodiments herein disclosed, since these embodiments are only intended as illustrations of several aspects of the invention. Any equivalent embodiment is intended to be within the scope of this invention. Various modifications of the invention in addition to those shown and described herein will become apparent to those skilled in the art from the foregoing description. Such modifications are also intended to fall within the scope of the appended claims.

EXAMPLE 1 a) A tank was filled with Sorbitol syrup (Sorbidex C*16100, from Cargill), dry substance=50%
b) NaOH solution was added, (NaOH=0.2% on db (dry base); pH>11
c) Followed by flowing through an heat exchanger (T=95° C.), and
d) Flowing through the column with the strong anionic resin MSA-1 BVH=0.5 (Bed volume/hour)

The results are displayed in Table 1.

TABLE 1

Temperature = 95° C.

| | | Feed Inlet | Outlet | |
|---|---|---|---|---|
| Hours | Days | R.S. (% db) | µS/cm | R.S. (% db) |
| 3 | 1 | 0.058 | / | 0.015 |
| 20 | 1 | 0.058 | 390 | 0.011 |
| 27 | 2 | 0.058 | 390 | 0.010 |
| 49 | 3 | 0.063 | 390 | 0.009 |
| 70 | 4 | 0.060 | 400 | 0.009 |
| 79 | 4 | 0.061 | 400 | 0.010 |
| 98 | 6 | 0.065 | 470 | 0.006 |
| 122 | 6 | 0.068 | 460 | 0.006 |
| 139 | 7 | 0.073 | 720 | 0.009 |
| 163 | 8 | 0.071 | 350 | 0.007 |
| 177 | 8 | 0.070 | 400 | 0.005 |
| 200 | 9 | 0.070 | 550 | 0.006 |
| 205 | 9 | 0.072 | 430 | 0.005 |
| 216 | 9 | 0.075 | 630 | 0.007 |
| 234 | 10 | 0.060 | 530 | 0.008 |
| 244 | 11 | 0.060 | 370 | 0.008 |
| 262 | 11 | 0.070 | 410 | 0.005 |
| 287 | 12 | 0.070 | 500 | 0.007 |
| 313 | 13 | 0.070 | 380 | 0.005 |
| 325 | 14 | 0.052 | 500 | 0.005 |
| 343 | 15 | 0.052 | 400 | 0.004 |
| 367 | 16 | 0.064 | 380 | 0.005 |
| 391 | 17 | 0.070 | 500 | 0.006 |
| 396 | 17 | 0.064 | 340 | 0.007 |
| 420 | 18 | 0.064 | 360 | 0.006 |
| 448 | 19 | 0.055 | 390 | 0.005 |
| 472 | 20 | 0.044 | 400 | 0.005 |
| 484 | 21 | 0.056 | 500 | 0.006 |
| 506 | 22 | 0.056 | 400 | 0.004 |
| 530 | 23 | 0.060 | 400 | 0.004 |
| 554 | 24 | 0.056 | 360 | 0.003 |
| 578 | 25 | 0.050 | 400 | 0.005 |
| 604 | 26 | 0.050 | 500 | 0.006 |
| 634 | 27 | 0.060 | 520 | 0.005 |
| 721 | 31 | 0.060 | 360 | 0.005 |

µS/cm = conductivity measured on the outlet anionic resin product (as is) with a "Sigma precision" Conductometer.
R.S. = reducing sugars measured according to the Copper method.

Copper Method 1) 50 g of the sample are combined with the copper solution. (Combined Copper-solution (e.g. B. Kraft, Art. No.: 3042)

2) The mixture has to be heated up to cooking within 3 minutes. After exactly 5 minutes of intensive cooking the reaction mixture is cooled down to 20° C.; for exact values the reflux condenser has to be rinsed with water.

3) 25 mL 5 N sulfuric acid are added to solution while stirring the mixture.

4) 1 mL of the starch solution (aqueous starch solution 1%) is added.

5) Mix thoroughly and titrate with 0.1 N sodium thiosulfate solution until colour changes to blue.

6) Titrate blank using same amount of ingredients as in determination solution.

7) Determine the dry substance content.

2) Quantification mL of consumed thiosulfate solution=(mL titration for blank−mL titration for sample)

From the appropriate table find the mg of dextrose equivalent to the mL of consumed 0.1 N thiosulfate solution.

Then calculate the reducing sugar content:

% reducing sugar=mg dextrose×10/g sample×dry substance(%)

TABLE

Determination of mg red. sugar as glucose by consumption of a 0.1 N sodium thiosulfate solution.

| ml | .0 | .1 | .2 | .3 | .4 | .5 | .6 | .7 | .8 | .9 |
|---|---|---|---|---|---|---|---|---|---|---|
| 0 | 0.0 | 0.8 | 1.4 | 1.8 | 2.1 | 2.5 | 2.9 | 3.2 | 3.5 | 3.8 |
| 1 | 4.1 | 4.3 | 4.6 | 4.9 | 5.2 | 5.6 | 5.9 | 6.2 | 6.5 | 6.7 |
| 2 | 7.0 | 7.3 | 7.7 | 8.0 | 8.3 | 8.6 | 8.8 | 9.1 | 9.3 | 9.5 |
| 3 | 9.8 | 10.1 | 10.4 | 10.6 | 10.9 | 11.2 | 11.5 | 11.8 | 12.1 | 12.4 |
| 4 | 12.7 | 13.0 | 13.2 | 13.5 | 13.8 | 14.1 | 14.4 | 14.7 | 14.9 | 15.1 |
| 5 | 15.4 | 15.7 | 16.0 | 16.3 | 16.6 | 16.8 | 17.0 | 17.3 | 17.6 | 17.9 |
| 6 | 18.2 | 18.5 | 18.7 | 19.0 | 19.3 | 19.6 | 19.9 | 20.2 | 20.5 | 20.8 |
| 7 | 21.0 | 21.3 | 21.6 | 21.9 | 22.2 | 22.5 | 22.8 | 23.0 | 23.3 | 23.6 |
| 8 | 23.9 | 24.2 | 24.5 | 24.8 | 25.0 | 25.3 | 25.6 | 25.9 | 26.2 | 26.5 |
| 9 | 26.8 | 27.2 | 27.4 | 27.7 | 28.0 | 28.3 | 28.6 | 28.9 | 29.2 | 29.5 |
| 10 | 29.8 | 30.1 | 30.4 | 30.7 | 31.0 | 31.3 | 31.6 | 31.9 | 32.2 | 32.5 |
| 11 | 32.8 | 33.1 | 33.4 | 33.7 | 34.0 | 34.3 | 34.6 | 34.9 | 35.2 | 35.5 |
| 12 | 35.8 | 36.1 | 36.4 | 36.7 | 37.0 | 37.3 | 37.6 | 37.9 | 38.2 | 38.5 |
| 13 | 38.8 | 39.1 | 39.4 | 39.7 | 40.0 | 40.2 | 40.5 | 40.8 | 41.1 | 41.4 |
| 14 | 41.7 | 42.0 | 42.2 | 42.5 | 42.8 | 43.1 | 43.4 | 43.8 | 44.1 | 44.4 |
| 15 | 44.6 | 44.9 | 45.2 | 45.5 | 45.8 | 46.1 | 46.4 | 46.7 | 47.0 | 47.3 |
| 16 | 47.6 | 47.9 | 48.2 | 48.5 | 48.8 | 49.1 | 49.4 | 49.7 | 50.0 | 50.3 |
| 17 | 50.6 | 50.9 | 51.2 | 51.5 | 51.8 | 52.1 | 52.4 | 52.7 | 53.0 | 53.3 |
| 18 | 53.6 | 53.9 | 54.2 | 54.5 | 54.8 | 55.1 | 55.4 | 55.7 | 56.1 | 56.4 |
| 19 | 56.7 | 57.0 | 57.3 | 57.6 | 57.9 | 58.2 | 58.5 | 58.8 | 59.1 | 59.4 |
| 20 | 59.7 | 60.0 | 60.3 | 60.6 | 60.9 | 61.2 | 61.5 | 61.8 | 62.1 | 62.4 |
| 21 | 62.7 | 63.0 | 63.3 | 63.6 | 63.9 | 64.2 | 64.5 | 64.8 | 65.1 | 65.4 |
| 22 | 65.7 | 66.0 | 66.3 | 66.6 | 66.9 | 67.2 | 67.5 | 67.8 | 68.1 | 68.4 |
| 23 | 68.7 | 69.0 | 69.3 | 69.6 | 69.9 | 70.2 | 70.5 | 70.8 | 71.1 | 71.4 |
| 24 | 71.7 | 72.0 | 72.3 | 72.6 | 72.9 | 73.2 | 73.5 | 73.8 | 74.1 | 74.4 |
| 25 | 74.7 | 75.0 | 75.3 | 75.6 | 76.0 | 76.3 | 76.6 | 77.0 | 77.3 | 77.6 |
| 26 | 77.9 | 78.2 | 78.6 | 78.9 | 79.2 | 79.5 | 79.8 | 80.1 | 80.4 | 80.7 |
| 27 | 81.0 | 81.3 | 81.6 | 81.9 | 82.2 | 82.5 | 82.8 | 83.1 | 83.4 | 83.7 |
| 28 | 84.0 | 84.3 | 84.6 | 84.9 | 85.2 | 85.6 | 85.9 | 86.2 | 86.5 | 86.8 |
| 29 | 87.2 | 87.5 | 87.8 | 88.1 | 88.4 | 88.7 | 89.0 | 89.4 | 89.7 | 90.0 |
| 30 | 90.4 | 90.7 | 91.0 | 91.3 | 91.7 | 92.0 | 92.3 | 92.7 | 93.0 | 93.4 |
| 31 | 93.7 | 94.1 | 94.4 | 94.8 | 95.1 | 95.4 | 95.8 | 96.1 | 96.5 | 96.9 |
| 32 | 97.2 | 97.5 | 97.8 | 98.2 | 98.5 | 98.9 | 99.3 | 99.6 | 99.9 | 100.2 |
| 33 | 100.6 | 100.9 | 101.3 | 101.7 | 102.0 | 102.3 | 102.6 | 103.0 | 103.4 | 103.7 |
| 34 | 104.1 | 104.4 | 104.7 | 105.0 | 105.4 | 105.8 | 106.1 | 106.5 | 106.8 | 107.1 |
| 35 | 107.4 | 107.8 | 108.2 | 108.5 | 108.9 | 109.2 | 109.5 | 109.9 | 110.2 | 110.6 |
| 36 | 110.9 | 111.3 | 111.6 | 111.9 | 112.3 | 112.6 | 113.0 | 113.3 | 113.7 | 114.0 |
| 37 | 114.3 | 114.7 | 115.0 | 115.4 | 115.7 | 116.1 | 116.4 | 116.7 | 117.1 | 117.4 |
| 38 | 117.8 | 118.1 | 118.5 | 118.8 | 119.1 | 119.5 | 119.8 | 120.2 | 120.6 | 120.9 |
| 39 | 121.2 | 121.5 | 121.9 | 122.2 | 122.6 | 123.0 | 123.3 | 123.6 | 123.9 | 124.3 |

EXAMPLE 2 a) A tank is filled with Maltitol syrup at ca. 96% purity (C* Maltidex H 16330, Cargill); dry substance=45%
b) NaOH solution was added, (NaOH=0.2% on db (dry base); pH>10.5
c) Followed by flowing through an heat exchanger (T=80° C.), and
d) Flowing through the column with the anionic resin BVH=0.5 (Bed volume/hour)

The results are displayed in Table 2.

TABLE 2

Flow: 0.5BVH
Temp = 80° C.

| | Feed Inlet | | Outlet | |
|---|---|---|---|---|
| Hours | Days | RS (% d.b.) | μS/cm (as is) | RS (% d.b.) |
| 3.0 | 1.00 | 0.30 | — | 0.000 |
| 6.0 | 1.00 | 0.30 | 541 | 0.004 |
| 9.0 | 1.00 | 0.22 | 496 | 0.000 |
| 15.5 | 1.00 | 0.22 | 523 | 0.000 |
| 32.5 | 2.00 | 0.22 | 522 | 0.015 |
| 37.5 | 2.00 | 0.22 | — | 0.016 |
| 40.0 | 2.00 | 0.22 | 515 | 0.005 |
| 80.5 | 4.00 | 0.28 | 508 | 0.016 |

TABLE 2-continued

Flow: 0.5BVH
Temp = 80° C.

| | Feed Inlet | | Outlet | |
|---|---|---|---|---|
| Hours | Days | RS (% d.b.) | μS/cm (as is) | RS (% d.b.) |
| 83.5 | 4.00 | 0.28 | 538 | 0.020 |
| 88.5 | 4.00 | 0.28 | 642 | 0.013 |
| 90.0 | 4.00 | 0.28 | 723 | 0.013 |
| 95.5 | 4.00 | 0.28 | 594 | 0.016 |
| 111.5 | 5.00 | 0.28 | 551 | 0.021 |
| 135.5 | 6.00 | 0.29 | 499 | 0.015 |
| 142.0 | 6.00 | 0.29 | 501 | 0.020 |
| 159.0 | 7.00 | 0.31 | 506 | 0.025 |
| 168.0 | 7.00 | 0.31 | 508 | 0.022 |
| 183.0 | 8.00 | 0.31 | 483 | 0.024 |
| 237.0 | 10.00 | 0.27 | 482 | 0.017 |
| 259.0 | 11.00 | 0.28 | 525 | 0.008 |
| 279.0 | 12.00 | 0.28 | 516 | 0.013 |
| 285.5 | 12.00 | 0.28 | 489 | 0.014 |
| 293.5 | 13.00 | 0.28 | 519 | 0.009 |
| 318.0 | 14.00 | 0.31 | 465 | 0.017 |
| 341.0 | 15.00 | 0.31 | 454 | 0.016 |
| 348.0 | 15.00 | 0.31 | 457 | 0.015 |
| 355.0 | 15.00 | 0.20 | 430 | 0.014 |
| 378.0 | 16.00 | 0.20 | 458 | 0.016 |
| 402.5 | 17.00 | 0.20 | 437 | 0.009 |
| 425.5 | 18.00 | 0.20 | 480 | 0.008 |

TABLE 2-continued

Flow: 0.5BVH
Temp = 80° C.

| | | Feed Inlet | Outlet | |
|---|---|---|---|---|
| Hours | Days | RS (% d.b.) | μS/cm (as is) | RS (% d.b.) |
| 433.5 | 19.00 | 0.20 | 443 | 0.011 |
| 455.5 | 19.00 | 0.13 | 424 | 0.013 |
| 475.0 | 20.00 | 0.13 | 428 | 0.014 |
| 490.0 | 21.00 | 0.13 | 416 | 0.011 |
| 506.5 | 22.00 | 0.09 | 432 | 0.010 |
| 544.5 | 23.00 | 0.09 | 417 | 0.007 |
| 551.0 | 23.00 | 0.09 | 471 | 0.005 |
| 577.5 | 25.00 | 0.06 | 420 | 0.010 |
| 598.0 | 25.00 | 0.16 | 412 | 0.01 |
| 606.5 | 26.00 | 0.16 | 383 | 0.01 |
| 625.0 | 27.00 | 0.16 | 399 | 0.011 |
| 647.5 | 27.00 | 0.10 | 448 | 0.010 |
| 671.5 | 28.00 | 0.10 | 445 | 0.014 |
| 692.5 | 29.00 | 0.12 | 470 | 0.013 |
| 721.5 | 31.00 | 0.12 | 477 | 0.014 |

COMPARATIVE EXAMPLE

Batch Process

1. Dry Substance of (Sorbidex C 16100, Cargill) was 50-55%, and the residual Sugars on db (dry base): 0.070-0.100%
2. NaOH was added in an amount of 0.4-0.9% on ds (dry substance)(pH>11.0)
3. Temperature was 80-100° C. and the retention time was between 4-8 hours After this treatment the sorbitol product (=polyol composition) had a Final Residual Sugars on db: <0.014%.

This example demonstrates the long reaction times (long contact time between polyol and alkaline medium) and the high consumption of NaOH.

COMPARATIVE EXAMPLE

Continuous Process without Feed of NaOH a) A tank was filled with Maltitol syrup at ca. 96% purity (C* Maltidex H 16330, Cerestar); the dry substance of the maltitol syrup was 45%
b) The syrup was flowing through an heat exchanger (T=80° C.), followed by
c) Flowing through the column with the anionic resin MSA-1, at a BVH=0.5 (Bed volume/hour).

The treatment had to be stopped after 3.3 days (79 hrs), as the R.S-value remained the same as the R.S value of the maltitol feed.

The invention claimed is:

1. A continuous process for preparing alkali- and heat-stable polyol compositions and said process comprises the following steps:
   a) taking an aqueous solution of a polyol composition comprising polyols and y % of reducing sugars based upon the dry substance of the polyol composition,
   b) adding to the aqueous solution an effective amount of alkali,
   c) feeding the aqueous solution to a resin battery comprising an anion exchange resin for obtaining an aqueous polyol composition comprising polyols and x % of reducing sugars based upon the dry substance of the polyol composition, wherein an effective amount of alkali is an amount where the resin battery is in full service mode for at least 30 days without regeneration mode, and wherein x<y,
   d) collecting the aqueous polyol composition comprising polyols and x % of reducing sugars based upon the dry substance of the polyol composition.

2. A process according to claim 1 characterized in that y % is from 0.050% to 0.300% based upon dry substance of polyol composition.

3. A process according to claim 1 characterized in that x % is not more than 0.040% based upon dry substance of polyol composition.

4. A process according to claim 1 characterised in that the resin battery is further comprising a cationic resin and a polisher resin.

5. A process according to claim 1 characterised in that the anion exchange resin is a strong base anion exchange resin in the hydroxide form.

6. A process according to claim 1 characterised in that the temperature of the resin battery is from 70 to 100° C.

7. A process according to claim 1 characterised in that the aqueous polyol composition, comprising polyols and x % of reducing sugars based upon the dry substance of the polyol composition, is increased in dry substance.

8. A process according to claim 1 characterised in that the polyol is sorbitol.

9. A process according to claim 1 characterised in that the polyol is maltitol.

10. A process according to claim 1 characterised in that a volume throughput is between 0.2 and 1 BV/hour.

11. A process according to claim 1 characterized in that x % is not more than 0.015% based upon dry substance of polyol composition.

12. A process according to claim 1 characterised in that the temperature of the resin battery is from 75 to 95° C.

13. A process according to claim 1 characterised in that the temperature of the resin battery is from 80 to 90° C.

14. A process according to claim 1 characterized in that the effective amount of alkali is from 0.1 to 0.5% based upon dry substance of polyol composition.

15. A process according to claim 1 characterized in that the effective amount of alkali is from 0.1 to 0.2% based upon dry substance of the polyol composition.

* * * * *